(12) United States Patent
Elsheikh et al.

(10) Patent No.: US 9,206,097 B2
(45) Date of Patent: Dec. 8, 2015

(54) METHOD TO PURIFY AND STABILIZE CHLOROOLEFINS

(75) Inventors: Maher Y. Elsheikh, Wayne, PA (US); Philippe Bonnet, Lyons (FR)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 13/509,843

(22) PCT Filed: Nov. 12, 2010

(86) PCT No.: PCT/US2010/056440
§ 371 (c)(1),
(2), (4) Date: May 15, 2012

(87) PCT Pub. No.: WO2011/060211
PCT Pub. Date: May 19, 2011

(65) Prior Publication Data
US 2012/0226081 A1    Sep. 6, 2012

Related U.S. Application Data

(60) Provisional application No. 61/261,498, filed on Nov. 16, 2009.

(51) Int. Cl.
*C07C 17/38*     (2006.01)
*C07C 17/389*    (2006.01)
*C07C 17/42*     (2006.01)

(52) U.S. Cl.
CPC ............ *C07C 17/389* (2013.01); *C07C 17/42* (2013.01)

(58) Field of Classification Search
CPC ...... C07C 17/389; C07C 19/08; C07C 21/18; C07C 21/06; C07C 19/01; C07C 21/12; C07C 21/04; C07C 17/395; C07C 17/38; C07C 17/42

USPC ................ 570/239, 238, 216, 177, 179, 262
See application file for complete search history.

(56) References Cited

U.S. PATENT DOCUMENTS

| | | | |
|---|---|---|---|
| 2,852,572 A * | 9/1958 | Shukys et al. ............... 570/239 |
| 3,789,580 A * | 2/1974 | Allemang et al. ............ 95/142 |
| 4,358,627 A | 11/1982 | Ameen et al. |
| 5,169,995 A * | 12/1992 | Crooker et al. ............. 570/111 |
| 5,169,996 A | 12/1992 | Crooker et al. |
| 5,221,697 A * | 6/1993 | Crooker et al. ............. 521/131 |
| 2003/0018225 A1 | 1/2003 | Klausmeyer |
| 2008/0045758 A1 | 2/2008 | Cohn et al. |
| 2010/0181524 A1 | 7/2010 | Elsheikh et al. |
| 2011/0196178 A1 | 8/2011 | Nyberg |

FOREIGN PATENT DOCUMENTS

| | | |
|---|---|---|
| EP | 309958 A2 * | 4/1989 |
| EP | 0309958 A2 | 4/1989 |
| EP | 0309958 B1 * | 1/1993 |
| WO | WO 2008127940 A1 * | 10/2008 |

OTHER PUBLICATIONS

Dilla, W. et al. Patent No. EP0309958B1, 1993, English translation.*
EP0309958A2, Apr. 1998, pp. 1-6; English translation.*

* cited by examiner

*Primary Examiner* — Jafar Parsa
*Assistant Examiner* — Medhanit Bahta
(74) *Attorney, Agent, or Firm* — Steven D. Boyd

(57) ABSTRACT

The present invention is directed towards a method of purification of chloroolefins having 3 carbons and to a method to provide stable compositions of chloroolefins having 3 carbons. The chloroolefins are purified via the use of a solid absorbents for the removal of decomposition product such as phosgene and/or phosgene precursory from the reaction of the chloroolefins with oxygen. The chloroolefins stabilized against an increase of the phosgene level via the addition of inhibitors to the chloroolefins.

5 Claims, No Drawings

METHOD TO PURIFY AND STABILIZE CHLOROOLEFINS

FIELD OF THE INVENTION

The present invention is directed towards a method of purification of chloroolefins having 3 carbons and to a method to provide stable compositions of chloroolefins having 3 carbons.

BACKGROUND OF THE INVENTION

The Montreal Protocol for the protection of the ozone layer mandates the phase out of the use of chlorofluorocarbons (CFCs). Materials more "friendly" to the ozone layer such as hydrofluorocarbons (HFCs) e.g. 134a replaced chlorofluorocarbons. The latter compounds have proven to be greenhouse gases, causing global warming and could be regulated by the Kyoto Protocol on Climate Change. Replacement materials are needed which are environmentally acceptable i.e. have negligible ozone depletion potential (ODP) and acceptable low global warming potential (GWP). These material which are useful as low GWP blowing agents for thermoset and thermoplastic foams, solvents, heat transfer fluids such as in heat pumps and refrigerants include but are not limited to, 2,3,3,3-tetrafluoropropene (1234yf), 1,3,3,3-tetrafluoropropene (1234ze), 3,3,3-trifluoropropene (1243zf), 1-chloro-3,3,3-trifluoropropene (1233zd), 2-chloro-3,3,3 trifluoropropene (1233xf). The process of manufacturing these materials typically involves processes of fluorination with HF of chloroolefins starting materials such as 1,1,2,3-tetrachloropropene (1230xa) for manufacturing 1234yf and/or 1233xf, 1,1,3,3-tetrachloropropene (1230za) for manufacturing 1234ze and /or 1233zd and 1,1,3-trichloropropene (1240za) for manufacturing 1243zf.

The present invention is directed towards a method of purification of chloroolefins having 3 carbons and a method to provide stable compositions of purified chloroolefins having 3 carbons such as 1,1,2,3-tetrachloropropene, 1,1,3,3-tetrachloropropene, 1,1,3-trichloropropene and mixtures thereof.

A first aspect of this invention includes a method of purification of chloroolefins having 3 carbons to provide chloroolefins free of decomposition product such as phosgene or phosgene precursors. Such phosgene free products can be stored in non-ferrous containers in the absence of oxygenated compounds without the need of stabilizing additives.

In a second aspect the present invention is directed towards a method of providing stable composition of chloroolefins having 3 carbons that do not appreciably decompose during storage or during their subsequent use.

In all aspects of this invention, the chloroolefins provided by the method of the present invention can be used in fluorination processes for the manufacture of Low GWP materials such as 2,3,3,3-tetrafluoropropene and 2-chloro-3,3,3-trifluoropropene from 1230xa, 1,3,3,3-tetrafluoropropene and the manufacture of 1-chloro-3,3,3-trifluoropropene from 1230za and the manufacture of 3,3,3-trifluoropropene from 1240za.

WO2009003165 discloses the stabilization of hydrofluoroolefins FIFO and/or hydrochlorofluoroolefins HCFO against degradation during storage, handling and use such by adding stabilizer(s) selected from free radical scavengers, acid scavengers, oxygen scavengers, polymerization inhibitors and mixtures thereof. U.S. Pat. No. 5,169,995 hydrochlorofluorocarbon HCFC 141b which is inhibited against decomposition with additives such as alpha-methylstyrene. U.S. Pat. No. 5,221,697 discloses the use of alumina to stabilize hydrochlorofluorocarbon HCFC 141b against decomposition during storage or use.

WO2008127940 describes the stabilization of tetrachloropropenes using an antioxidants such as a phenolic antioxidant including p.methoxyphenol or p.tert.amylphenol. The inhibitors are solid materials that makes handling on a commercial scale difficult to implement. Furthermore these inhibitors require the use of MONEL® alloy for the vessels to minimize the formation of acid or phosgene.

SUMMARY OF THE INVENTION

This present invention is directed towards a method of purification or stabilization of chloropropene and/ or chloropropane. The purification provides for stable compositions of chloropropenes such as 1,1,2,3-tetrachloropropene (1230xa), 1,1,3,3-tetrachloropropene (1230za), 1,1,1,2-tetrachloropropene (1230x1), 1,1,3-trichloropropene (1240za) and chloropropanes such as 240db 1,1,1,2,3-pentachloropropane, 240ab 1,1,1,2,2-pentachloropropane or mixtures thereof. The method of the present invention provides stable, purified chloroolefins compositions which are particularly useful for the manufacture of HFOs and HCFOs such as 1234yf, 1233xf, 1234ze, 1233zd and 1243zf

DETAILED DESCRIPTION OF THE INVENTION

Phosgene, $COCl_2$, is a hazardous material commonly produced during the manufacturing, processing, shipping or storage of chloroolefins and/or chloroalkanes having 2-6 carbon atoms in ferrous containers. The process of forming phosgene, takes place by the addition of oxygen to the olefin to form the 1,2-dioxetane intermediate followed by decomposition of the latter compound to carbonyl containing compounds such phosgene $COCl_2$ and carboxylic acid chloride, as shown in Scheme 1:

Scheme 1: Formation of phosgene in 1230xa

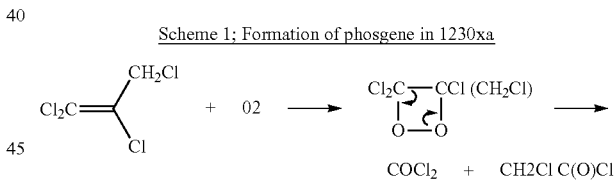

A similar degradation mechanism occurs when 1230za or 1240za or 1230xf, are stored or manufactured in ferrous containers. The formation of phosgene can also occur when the precursor to the chloroalkenes, such as 240db $CCl_3CHOCH_2Cl$ in case of 1230xa is exposed to oxygen containing gas when stored in a ferrous container. Scheme 2 shows a typical reaction sequence.

Scheme 2: Formation of phosgene in 240db, stored in ferrous container.

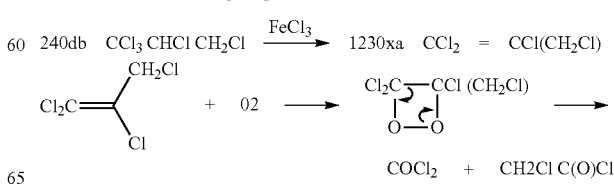

In a first aspect, the present invention is directed towards the use of a solid adsorbent for the removal of decomposition products such as to phosgene, acids such as HCl and/or carboxylic acid, from the reaction of chloroolefins and/or chloroalkanes having 3 carbons, with oxygen. Preferably, the solid adsorbents are selected from high surface area alumina, $Al_2O_3$, activated carbon or mixtures thereof. The adsorbent is preferably subjected to a drying process such as being placed under vacuum or heating to eg 100-200° C., under vacuum, until no more moisture is desorbed from the solid adsorbent. Preferably the surface area of the resulting dry adsorbent varies from about 10 to 4000 $m^2/g$ and porosity varies from about 0.005 to 0.5 $cm^3/g$.

This aspect of this invention provides for the removal of phosgene or phosgene precursors with the solid absorbent and allows for the storage of chloroolefins/chloroalkanes in non-ferrous containers without the need for the addition of any further stabilization additives.

In a second aspect, the invention is directed towards the addition of inhibitors capable of stabilizing chloroolefins and/or chloroalkanes having 3 carbons against an increase of the phosgene level. Preferred inhibitors are selected from the group consisting of α-methyl styrene, α-pineneoxide, β-pineneoxide, 1,2-epoxy butane, 1,2-hexadecene oxide, oxygen scavengers such as DEHA (diethylhydroxylamine), HQ (hydroquinone), MEKO (methylethylketooxime), p-methoxyphenol and the like and mixtures thereof. The level of the inhibitors can vary from about 20 ppm to 5% weight and preferably from about 50 ppm to 2 weight %.

This method prevents the formation of phosgene and/or acids from a decomposition reaction of the chloroolefins and/or chloroalkanes with oxygen even if stored in ferrous containers.

This present invention also provides a benefit during the use of the chlorinated propene and/or chlorinated propane in fluorination processes by providing stability for the chlorinated propene and/or chlorinated propane. In particular the present invention provides for purified and stabilized chlorinated propene and/or chlorinated propane such as 1230xa or 240db for use in the catalyzed fluorination to 1233xf. The latter compound can be used as the feedstock for the manufacturing of low GWP products such as 1234yf. The present invention also provides stable and purified chlorinated propene and/or chlorinated propane such as 1230za which is useful in the production of 1233zd and 1234ze

EXAMPLES

Method Used for the Quantification of Phosgene and Anhydrous $FeCl_3$

Hydrochloroolefin 1230xa can be analyzed to determine the presence of anhydrous $FeCl_3$ using inductive coupling plasma mass spectrometry (ICP). A typical contamination level is 2 ppm of anhydrous $FeCl_3$. The presence of phosgene can be determined by colorimetric testing using 4-(p-nitrobenzyl)-pyridine as described in A. L. Linch, et al., Am. Ind. Hyg. Ass. J. 26 (5), 465-73, 1965. A typical contamination level is 17 ppm of phospene. The measured absorption can be used to calculate the ppm level of phosgene against a calibration curve. The effect of the inhibitor in accordance with the present invention can be evaluated using an accelerated aging test comprising subjecting the contaminated 1230xa to UV irradiation for 5 hours. This is estimated to be equivalent to aging of 1230xa at room temperature for one year. The following prophetic examples outline the results expect from use of inhibitors/stabilizers in accordance with the present invention.

Example 1

Batch Purifications of 1230xa, Using Activated Alumina

Chloroalkene 1230xa (120 grams, containing phosgene 14ppm) could be mixed with 50 grams of a variety of commercially available dried activated alumina such as La Roche A201, A204 and BASF AL-4126 016 and analyzed after approximately one-half hour at room temperature. Analysis of phosgene can be carried out spectrophtometrically, using 4-(p-nitrobenzyl)-pyridine. It would be expected to show that the phosgene level would be reduced to less than about 1 ppm.

Example 2

Continuous Absorption of Phosgene from 1230xa Using Alumina

Chloroalkene 1230xa, containing about 14 ppm phosgene could be fed at a rate of about 20 ml/min at room temperature, through a fixed bed of about 85 grams of a LaRoche 204 or BASF AL-4126 E/16. The contact time would be about 5.3 minutes. For each of the alumina tested phosgene level of less than about 4 ppm would be expected.

Example 3

Effect of Contact Time on the Absorption of Phosgene

Example 2 with La Roche 204 alumina could be repeated with about 8 grams of activated alumina and a contact time of about 53 minutes. The phosgene level would be expected to be was reduced to about 4 ppm. At a contact time of about 26 minutes the phosgene level would be expected to be was reduced to about 1 ppm.

Example 4

Test of 1230xa Chemical Stability

The alumina treated 1230xa from Example 2, containing about 5 weight % of alpha-methyl styrene, could be subjected to UV irradiation for about five hours in the presence of air, simulating about one year of aging at ambient temperature. Analysis would be expected to show no evidence of phosgene formation. In contrast, if untreated 1230xa would be irradiated under similar conditions, about 20 ppm of phosgene would be expected to form.

Example 5

Stabilization of 1230xa against Phosgene Formation in the Presence of Inhibitors, Alpha-Methyl Styrene AMS, 1,2-Epoxy Butane EB, Alpha-Pinene Oxide APO, Beta-Pinene Oxide BPO, Diethylhydroxylamine DEHA Aerosol glass bottles would be filled with inhibitor (if any) impure 1230xa containing about 17 ppm phosgene and about 2 ppm $FeCl_3$. The bottles would be capped, air admitted to the bottles up to about 30 psig and the bottles would be placed in a box so as to form a ring. The ring would be slowly circulated and irradiated with a HANOVIA high pressure mercury arc for about 5 hours. Analysis of the samples for the presence of phosgene, using a calorimetric test with 4-(p-nitrobenzyl)-pyridine indicator, would be expected to show an increase of phosgene level in the samples containing no inhibitors, while the samples containing inhibitors, would show no increase in the phosgene level. Table 1 summarizes the expected results.

TABLE 1

Expected effect of various inhibitors on the chemical stability of impure 1230xa

| Inhibitor added .5 weight % | Zero hours of irradiation | After 5 hours UV irradiation |
|---|---|---|
| None | 17 | 32 |
| AMS | 17 | 16 |
| EB | 17 | 15 |
| ABO | 17 | 16 |
| BPO | 17 | 17 |

Repeating this test using purified 1230xa (as in Example 2) containing no inhibitor, would be expected to show a substantial formation of phosgene, whereas samples containing inhibitors, would be expected to show excellent stability of 1230xa. Table 2 summarizes the expected results.

TABLE 2

Expected effect of various inhibitors on the chemical stability of purified 1230xa

| Inhibitor added .5 weight % | Zero hours of irradiation | After 5 hours UV irradiation |
|---|---|---|
| None | 0 | 18 |
| AMS | 0 | .25 |
| EB | 0 | .23 |
| ABO | 0 | .24 |
| BPO | 0 | .24 |
| DEHA | 0 | .12 |

What we claims:

1. A method of removing and inhibiting the formation of decomposition products of oxygen and chloroolefins and/or chloroalkanes having 3 carbons from chloroolefins and/or chloroalkanes having 3 carbons selected from the group consisting of 1,1,2,3-tetrachloropropene (1230xa), 1,1,3,3-tetrachloropropene (1230za), 1,1,1,2-tetrachloropropene (1230xf), 1,1,1,2,3-pentachloropropane (240db), 1,1,1,2,2-pentachloropropane (240ab) and mixtures thereof during storage in ferrous containers comprising contacting said chloroolefins and/or chloroalkanes with a water free, solid adsorbent selected from the group consisting of $Al_2O_3$, activated carbon and mixtures thereof having a surface area of from about 10 to 4000 $m^2/g$ and a porosity from about 0.005 to 0.5 $cm^3/g$; and adding to said chloroolefins and/or chloroalkanes an inhibitor selected from the group consisting of α-methyl styrene, α-pineneoxide, β-pineneoxide, 1,2-hexadecene oxide, and mixtures thereof.

2. The method of claim 1 wherein said decomposition products comprise phosgene, phosgene precursors and acids.

3. The method of claim 2 wherein said acids comprise carboxylic acids and HCl.

4. The method of claim 1 wherein water is removed from said solid adsorbent prior to said contacting by heating and/or placing said solid adsorbent under a vacuum.

5. The method of claim 1 wherein said inhibitor is added in an amount from about 20 ppm to about 5 wt % of said chloroolefins and/or chloroalkanes.

* * * * *